United States Patent
Menon et al.

(10) Patent No.: US 11,793,502 B2
(45) Date of Patent: Oct. 24, 2023

(54) CLOSING DEVICE FOR AN OPENING IN THE HEART OF A PATIENT

(71) Applicant: Berlin Heart GmbH, Berlin (DE)

(72) Inventors: Ares K. Menon, Berlin (DE); Michael Matthes, Altlandsberg (DE)

(73) Assignee: Berlin Heart GmbH, Berlin (DE)

( * ) Notice: Subject to any disclaimer, the term of this patent is extended or adjusted under 35 U.S.C. 154(b) by 675 days.

(21) Appl. No.: 16/487,414

(22) PCT Filed: Feb. 22, 2018

(86) PCT No.: PCT/EP2018/054447
§ 371 (c)(1),
(2) Date: Aug. 20, 2019

(87) PCT Pub. No.: WO2018/154025
PCT Pub. Date: Aug. 30, 2018

(65) Prior Publication Data
US 2020/0054311 A1    Feb. 20, 2020

(30) Foreign Application Priority Data
Feb. 23, 2017    (EP) .................................... 17157732

(51) Int. Cl.
*A61B 17/00*    (2006.01)
*A61B 5/021*    (2006.01)
(Continued)

(52) U.S. Cl.
CPC .......... *A61B 17/0057* (2013.01); *A61B 5/021* (2013.01); *A61N 1/3627* (2013.01);
(Continued)

(58) Field of Classification Search
CPC ...... A61B 17/0057; A61B 2017/00022; A61B 2017/00221; A61B 2017/00411;
(Continued)

(56) References Cited

U.S. PATENT DOCUMENTS

| 10,207,088 B2 | 2/2019 | Osypka |
| 2009/0227938 A1 | 9/2009 | Fasching et al. |

(Continued)

FOREIGN PATENT DOCUMENTS

| CN | 101687092 A | 3/2010 |
| CN | 103747815 A | 4/2014 |

(Continued)

OTHER PUBLICATIONS

International Search Report, issued in International Application PCT/EP2018/054447, dated May 8, 2018, pp. 1-3, European Patent Office, Rijswijk, Netherlands.

(Continued)

*Primary Examiner* — Mohamed G Gabr
(74) *Attorney, Agent, or Firm* — Crowell & Moring LLP (57) ABSTRACT

A closing device is provided for an opening in the heart of a patient, the closing device comprising a ring, which can be fastened to the body tissue of the heart in the region of the opening. The ring has a ring opening. The closing device further comprises a closing element, which can be inserted into the ring opening in order to close the ring opening. Furthermore, the closing element can have at least two integrated sensors. The elements provided in or on the closing element can be connected to and can interact with monitoring and control devices in different ways.

14 Claims, 10 Drawing Sheets

(51) Int. Cl.
  *A61N 1/362* (2006.01)
  *A61N 1/372* (2006.01)
  *A61N 1/39* (2006.01)
(52) U.S. Cl.
  CPC ........... *A61N 1/372* (2013.01); *A61N 1/3962* (2013.01); *A61N 1/3968* (2013.01); *A61B 2017/00022* (2013.01); *A61B 2017/0061* (2013.01); *A61B 2017/00221* (2013.01); *A61B 2017/00659* (2013.01); *A61B 2017/00734* (2013.01)
(58) Field of Classification Search
  CPC .. A61B 2017/00575; A61B 2017/0061; A61B 2017/00659; A61B 2017/00663; A61B 2017/00734; A61B 2017/00862; A61B 2090/064; A61B 5/021; A61B 90/40; A61N 1/3627; A61N 1/372; A61N 1/37512; A61N 1/3962; A61N 1/3968; A61N 1/3993
  See application file for complete search history.

(56) References Cited

U.S. PATENT DOCUMENTS

2012/0022562 A1    1/2012  Willard
2016/0045165 A1*   2/2016  Braido ............. A61B 17/12122
                                                        623/2.1
2016/0325079 A1   11/2016  Osypka

FOREIGN PATENT DOCUMENTS

EP         3 090 766 A1    11/2016
WO    WO 2005/013832 A1     2/2005
WO    WO 2008/094468 A2     8/2008

OTHER PUBLICATIONS

Office Action for China Patent Application No. CN 201880013664.8 dated May 31, 2022 (17 pages).

* cited by examiner

CLOSING DEVICE FOR AN OPENING IN THE HEART OF A PATIENT

CROSS-REFERENCE TO RELATED APPLICATIONS

This application is a 371 nationalization of international patent application PCT/EP2018/054447 filed Feb. 22, 2018, which claims priority under 35 USC § 119 to European patent application 17157732.3 filed Feb. 23, 2017. The entire contents of each of the above-identified applications are hereby incorporated by reference.

DETAILED DESCRIPTION

The invention is in the field of precision engineering, electronics, signals processing, and is in the field of medical technology and may be used particularly advantageously in an implanted closing device for an opening in the heart of a patient.

A pump for supporting cardiac function is frequently used in patients having certain heart defects. Such a pump is frequently connected to a heart ventricle, for instance the left ventricle, by means of an artificially added opening, so that the load on the heart may be relieved using the pump implanted in or operated outside of the body.

In some patients, the heart recovers with the influence of the heart support so that the pump may then be removed if certain withdrawal criteria are satisfied. To this end, the pump or pump connector is removed from the opening in the heart chamber or from the suture ring fastened there, and the ring opening thus left behind in the suture ring must be closed. A number of closing elements that are inserted into the suture ring as tightly as possible are already known for closing such a suture ring.

The underlying object of the present invention is to provide a closing device for an opening in the heart of a patient that has additional functions.

The invention consequently relates to a closing device for an opening in the heart of a patient having a ring that can be fastened to the body tissue of the heart in the region of the opening and having a ring opening, and having a closing element that may be added to the ring opening to close the latter, the closing element having at least one integrated sensor.

Such a closing element may be embodied, for example, as a cylindrical or slightly conical stopper that may be inserted or tightly pressed into a circular opening in a ring/suture ring. In principle the closing element may have a device for radial expansion in the ring opening, so that the closing element may be added to the ring in a sealing manner.

The closing element may be embodied, for example, as a silicone stopper or may comprise, at least in part, silicone or another elastomer. There is room for at least one sensor or even for two or more sensors in the volume of the closing element. The sensors or even additional actuators may project out of the closing element, may be arranged on the outer side of the closing element, or may at least border the outer side of the closing element, so that physical measured variables outside of the closing element may be detected by the sensors or so that elements outside of the closing element may be acted upon by an actuator integrated into the closing element.

The ring that may be fastened in the region of the opening of the heart may be embodied as a suture ring that has, for example, a metal subring and a suturable subring comprising, in particular, a textile fabric. The suturable ring is generally embodied like a flange so that it is positioned on the outside on the edge of the opening in the heart and there may be sutured to the heart tissue by means of a suture. The metal subring may be embodied, for example, as a connector and may be welded or glued to the suturable subring.

The closing element may also comprise a strong, rigid, or inelastic material in its radially inner region and may have an elastomer ring in its radially outer region.

The closing element may comprise, for example, two axially opposing compressible disks or ring-shaped elements, between which a ring-shaped sealing element is arranged axially compressible and thus radially expandable.

The ring-shaped sealing element may comprise an elastomer, for example, and may be embodied as solid elastomer or as elastomer foam, or it may have a hollow chamber, in particular an inflatable hollow chamber that may be filled with gas or fluid.

The metallic separating ring of the suture ring is normally embodied complementary to the closing element such that a fluid-tight and permanent connection may be produced between the closing element and the suture ring.

In one embodiment of the invention it may be provided that at least two sensors integrated into the closing device are designed for detecting a time-dependent pressure. Such a sensor may be arranged, for example, in a hollow chamber of the closing element, the hollow chamber being sealed by a thin and movable membrane that reacts to changes in pressure so that the pressure acting outside of the closing element is transmitted to the pressure in the hollow chamber of the closing element. The pressure sensor may also be uncovered relative to the exterior of the closing element and may detect the pressure in the vicinity of the closing element directly.

In addition, in one embodiment it may be provided that the closing element has at least one pressure sensor that detects a pressure on a first outer side of the closing element, and has in particular a second pressure sensor that detects a pressure on a second outer side, the closing element being designed such that when the closing element is in the closing position the first outer side faces the interior of the heart and the second outer side faces the exterior of the heart.

In another embodiment, the closing element may also have a differential pressure sensor that is connected to side facing the interior of the heart in operation and to the side facing the exterior of the heart using a gas connection or by means of a membrane so that a membrane of this sensor measures the differential pressure directly.

The closing element generally has a target position for sealing in the ring opening of the closing device so that one side of the closing element is provided to be inserted through the ring opening into the interior of the heart, while the opposing side of the closing element faces the heart exterior-side of the ring. If two pressure sensors are provided, they may detect the pressure in the interior of the heart, on the one hand, and outside of the heart, on the other hand. Since the absolute pressure in the interior of the heart can only be determined by finding the difference to the pressure in the vicinity of the heart, such a dual pressure measurement for determining the absolute pressure in the heart is useful.

In another embodiment it may be provided that the closing element has one sensor or at least two sensors for detecting a voltage signal. Such sensors are generally made of metal and act either as antennas or as electrodes. If they are embodied as antennas, together with other electrically conducting elements outside of the closing device they form a capacitor via which a voltage may be coupled in. If the sensors are embodied as electrodes, they are accessible, for example, on the outside of the closing element and may be brought into contact with a body fluid or a body tissue such that they can detect electrical signals.

For example, it may be provided that the closing element has at least one electrode, in particular at least two electrodes, which form a surface region of the closing element, in particular a cylindrical or partially cylindrical surface region of the closing element, in at least one or at least two sub-regions. Each electrode may extend as a cylinder segment via a circumferential segment of the closing element.

The cylindrical or partially cylindrical electrodes may be placed into the surface of the closing element and may detect voltage potential in the tissue of the heart, for example in the region of the closing element, which projects through the ring to the interior of the heart. Such electrodes may also, however, transmit voltage pulses to the heart tissue, for instance from a cardiac pacemaker or a defibrillator.

In another embodiment of the invention it may also be provided that the closing element has at least one electrode, in particular at least two electrodes, that each have first part arranged inside the closing element and a second part that projects out of the closing element, the second part having a tip. In this case the tips of the electrodes may project into the heart tissue and thus produce an electrical connection to the heart tissue.

Thus it may be provided, for example, that an actuator integrated into the closing element has an electrode that may be acted upon with a time-dependent voltage signal and that may be connected in particular to a control device.

In addition, in a closing device it may be provided that at least one or two sensors and/or at least one actuator may be connected, by means of a cable or a non-wired transmitting device, to a control or monitoring device, directly or by means of an integrated preprocessing device integrated into the closing device, in particular into the closing element.

Thus, one or a plurality of the sensors and/or actuators that are integrated into the closing element, for example, may be connected to a control and monitoring device by means of a cable. The control or monitoring device may be disposed inside or outside of the closing element or closing device, for example may also be part of the closing device or may also be provided outside of the closing device. The connection may be realized either by means of a cable or by means of a non-wired transmitting device, in this case the sensor and/or the actuator or even a plurality of sensors and/or actuators being connected to a transmitting device and/or a receiving device that communicates with a complementary transmitting and/or receiving device, for example via a radio signal or another non-wired communication connection. Possible types of connections are a radio connection by means of Bluetooth or a similar standard, or a classic radio connection having frequency or amplitude modulation or one of the known digital radio interfaces. Communication via waveguide, ultrasound, infrared, or other transmission path is also possible, however.

For the purpose of signal transmission, it is possible to provide in the closing device, especially in the closing element itself, a preprocessing device that is connected directly to the sensor or actuator, for example by means of a cable, and that itself is connected to a transmitter or receiver that communicates inside or outside of the closing device via a non-wired transmission segment to a conductor or even via a wired transmission segment.

A preprocessing device can forward or process signals from a sensor directly, for instance in that parameters of a elapsed time of the detected variable are detected and forwarded. The preprocessing device may also undertake any other possible type of data processing or signal preparation, however, such as, for example, amplifying or attenuating the signals or filtering the signals.

For example, the preprocessing device can detect the temporal curve of the pressure differential between two pressure values measured on different sides of the closing device or of the closing element.

Another embodiment may be provided such that at least one sensor and/or at least one actuator may be or is connected to an energy storage element that is provided either implanted inside the body of the patient or outside the body of a patient. The energy storage element may be present in the form of a battery, in particular a rechargeable battery, inside of the closing element or outside of the closing element, as part of the closing device, or even outside of the closing device. The energy storage element may supply one or a plurality of sensors or actuators with energy for their functioning. The energy storage element may also supply a preprocessing device with energy. If an actuator is embodied as part of a defibrillator, the energy storage element may supply the actuator with the energy necessary for a shock process on the cardiac muscle.

It may also be provided that the energy storage element is integrated into the closing element or into an implantable/implanted control or monitoring device or is implanted as a module in the body of the patient. The energy storage element may be rechargeable from outside the body of the patient by means of a cable connection or inductively using magnetic action through the skin of the body of the patient. The energy storage element may also be formed, for example, as a part of a cardiac pacemaker or defibrillator or other implantable device.

Another embodiment may provide, for example, that the energy storage element is designed and arranged such that it may be recharged by means of an induction device arranged outside the body of the patient.

In addition to a closing device of the type cited in the foregoing, the invention relates to an implantable device having such a closing device, wherein the implantable device may also have in particular an energy storage element and/or a monitoring device and/or a control device. The monitoring device may be an implantable device for detecting electrocardiograms, for example, and the control device may be embodied as a cardiac pacemaker or defibrillator. The aforesaid devices may also be a direct part of the closing device and may be arranged, for example, in the closing element or on the closing element, in particular may be integrated into the closing element. Especially in this case, the connection to sensors and/or actuators in the closing element is not complicated.

A cardiac pacemaker and/or defibrillator is connected to one or a plurality of electrodes and is either integrated into the closing element or arranged outside of the closing element and connected to the appropriate electrodes by means of cables.

In addition to a closing device and an implantable device, the invention also relates to a method for operating an implantable device of the type described in the foregoing, it furthermore being provided that, when implanted, a pressure curve in a heart ventricle, in particular the left ventricle, is measured continuously by means at least one pressure sensor integrated into the closing element and from this an end diastolic filling pressure is determined continuously, or alternatively or in addition, also on the left or right atrium or on the right ventricle, and/or that, when implanted, an electrical signal or an energy pulses is emitted to the cardiac muscle by means of at least one electrode integrated into the closing element.

In one case, a pressure sensor integrated into the closing element determines the time-dependent pressure in a heart chamber, wherein the end diastolic filling pressure may be determined from the pressure curve. To this end, the differential pressure between the inner heart side and the outer heart side of the closing device is advantageously determined. The differential pressure curve may be used for determining the end-diastolic filling pressure. The end diastolic filling pressure is found by processing the data for the pressure curve either in the preprocessing device or in a monitoring device.

It may also be provided that electrical pulses are continuously detected and processed by means of one or a plurality of electrodes integrated into the closing element and that it is determined from the pulses whether an energy pulse should be emitted to the cardiac muscle by means of a defibrillator. If this is the case, the appropriate energy pulse is emitted to the cardiac muscle in the form of a voltage surge by means of an electrode integrated into the closing element.

In summary, it may be found that the present design permits the provision of one or a plurality of sensors and/or one or a plurality of actuators in or on a closing element of a closing device, wherein the sensor(s) and/or actuator(s) may be connected to monitoring or control devices that may be provided inside or outside of the closing element as well as inside or outside of the closing device and even inside or outside of the body of the patient. Corresponding signals transmission paths may be realized using non-wired cable or signals. Energy may be supplied to sensors and actuators in a variety of ways via an energy storage element that may either be integrated into a closing element or into the closing device or that may be present outside of the closing device. The energy storage element may also supply a monitoring and/or control device and may optionally be rechargeable, in particular may be inductively rechargeable.

The aforesaid features may be combined with one another in various configurations, as depicted using the figures listed and explained in the following.

Figure 1:
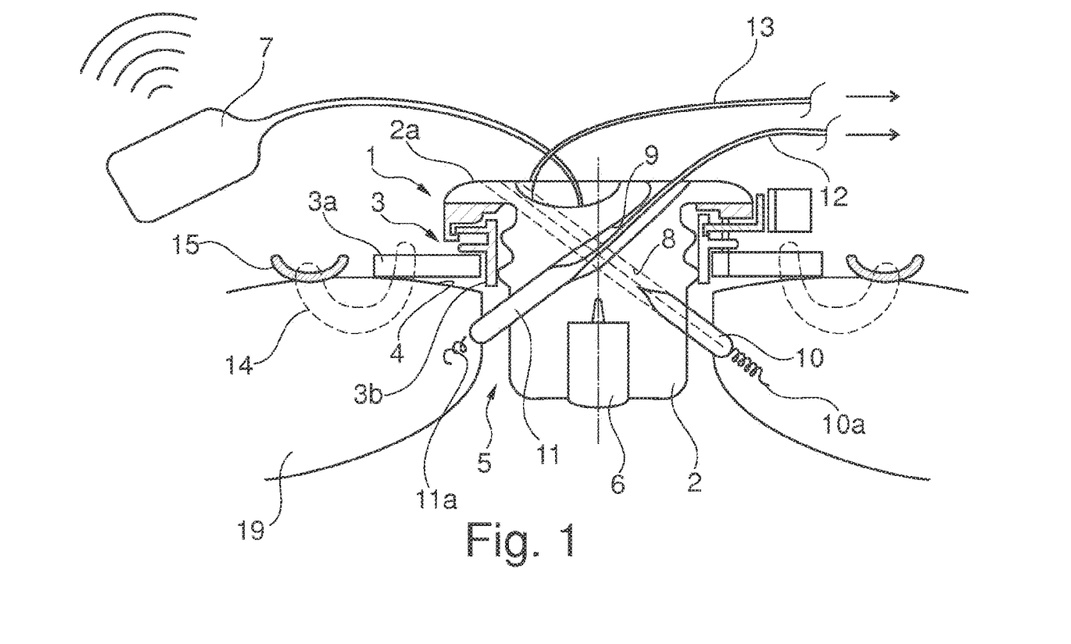
FIG. 1 is a longitudinal section of a first embodiment of a closing device.
Figure 2:
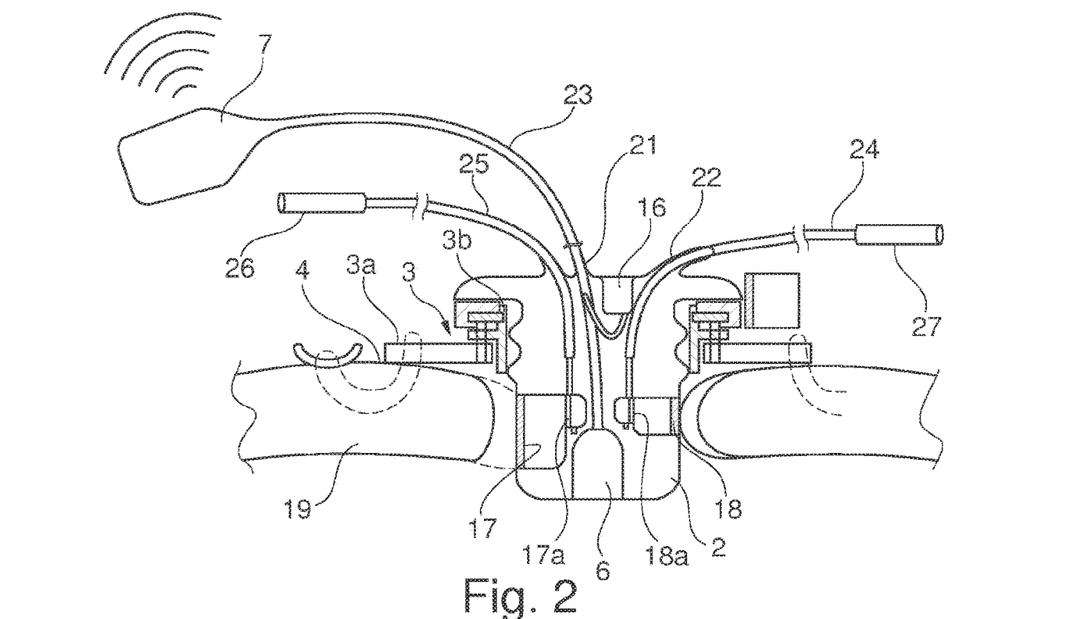
FIG. 2 is a longitudinal section of a second embodiment of a closing device.
Figure 3:
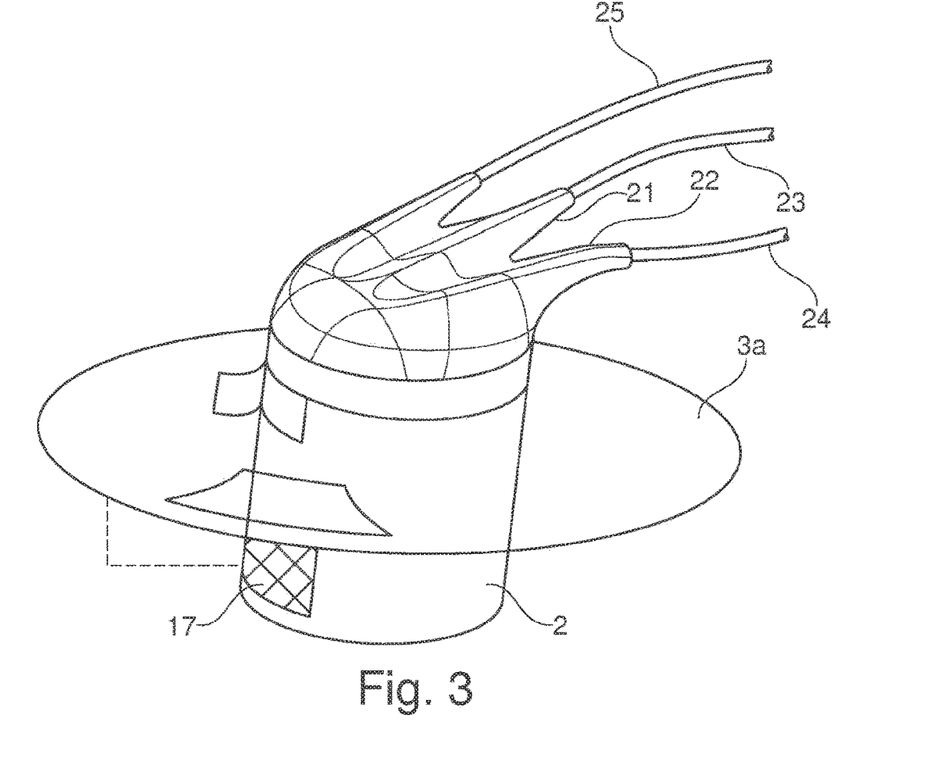
FIG. 3 is a three-dimensional view of a closing device.
Figure 4:
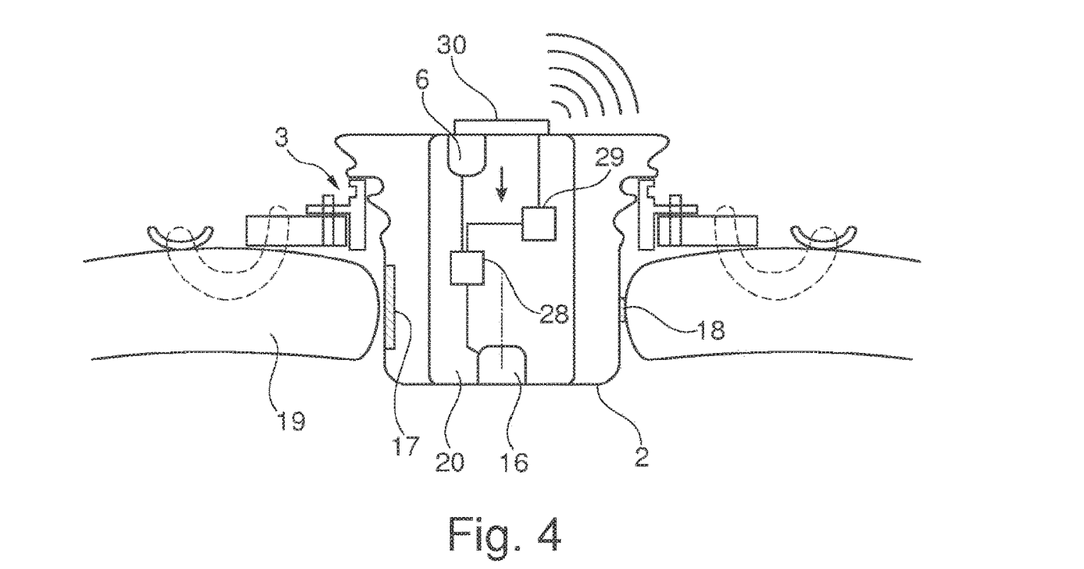
FIG. 4 depicts another embodiment of a closing device.
Figure 11:
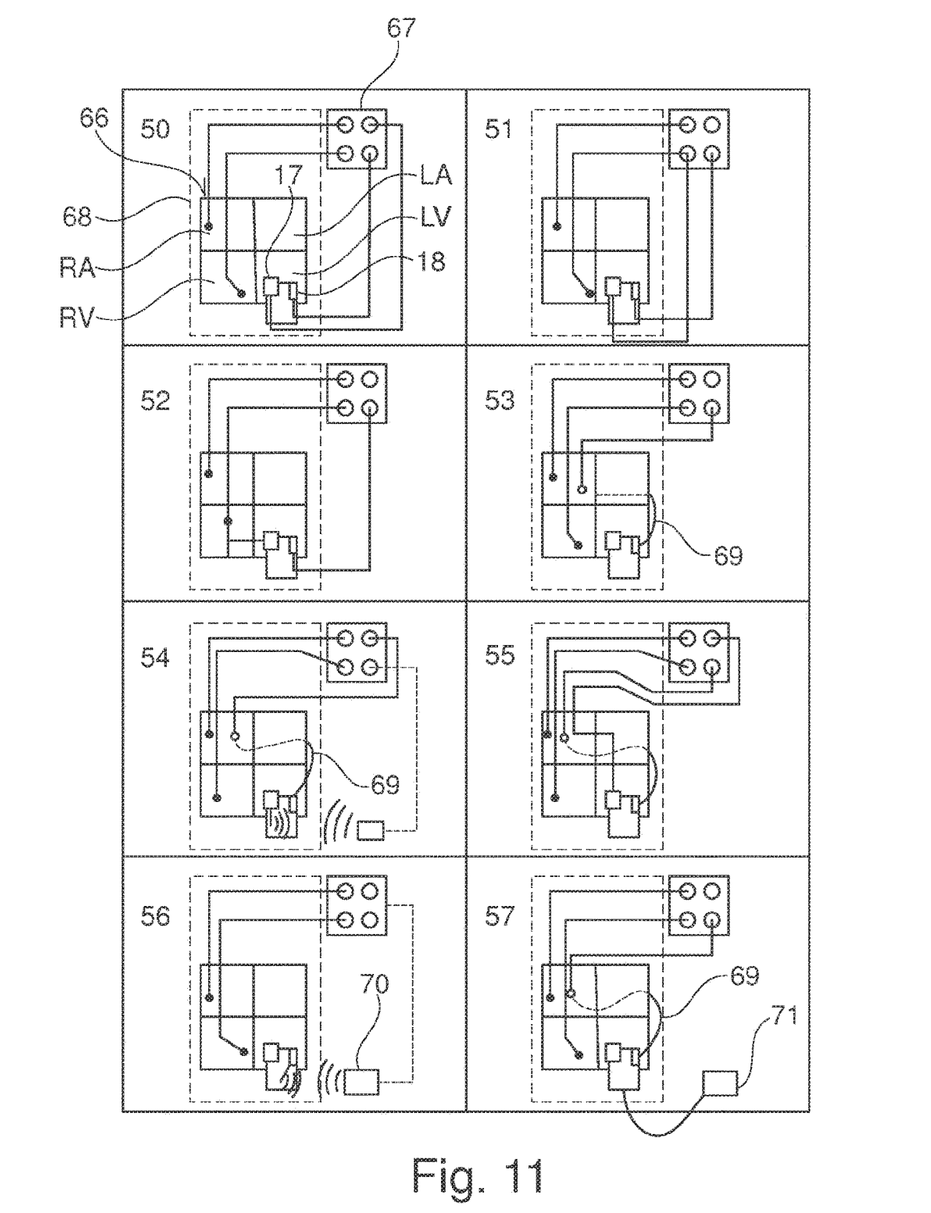
FIG. 11 depicts a first group of connection schemes; and,
FIG. 12 depicts a second group of connection schemes.
Figure 12:
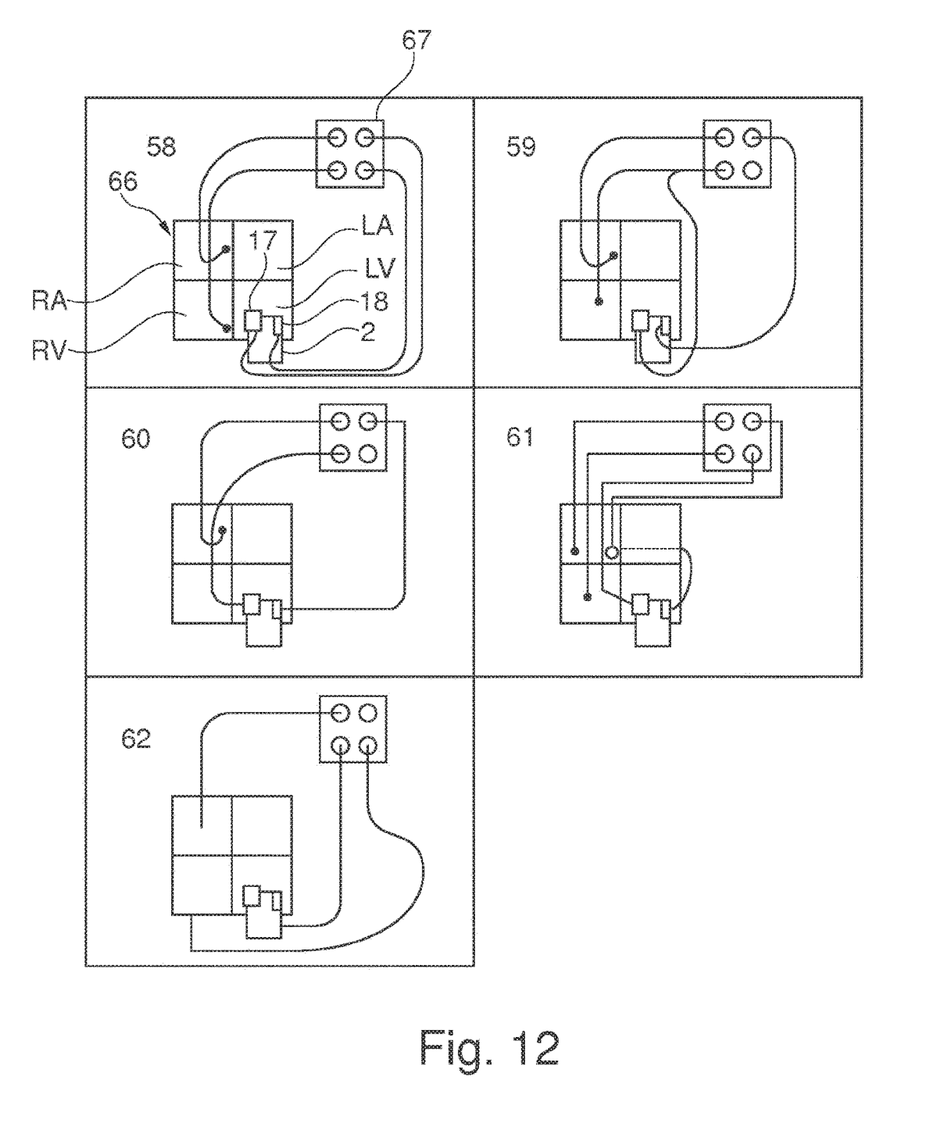

FIG. 1 is a longitudinal section of a first embodiment of a closing device;

FIG. 2 is a longitudinal section of a second embodiment of a closing device;

FIG. 3 is a three-dimensional view of a closing device;

FIG. 4 depicts another embodiment of a closing device;

FIGS. 5-10 depict different implantation scenarios for closing devices;

FIG. 11 depicts a first group of connection schemes; and,

FIG. 12 depicts a second group of connection schemes.

FIG. 1 depicts a longitudinal segment of a closing device 1 having a closing element 2 in the form of a silicone stopper and having a ring 3 that may be fastened on the edge 4 of an opening 5 in the heart of a patient. A pressure sensor 6 that, when implanted, faces the heart chamber/interior of the heart, depicted at the bottom of FIG. 1, is integrated into the silicone stopper 2/closing element. The pressure sensor 6 detects in a time-dependent manner the pressure curve for the blood in the heart and forwards these signals to a transmitter 7, which may be embodied, for example, as a Bluetooth transmitter, and which transmits the signals by means of radio waves to a Bluetooth receiver that may be arranged inside the body of the patient or outside the body of the patient and that itself may be connected to a monitoring device. The pressure sensor 6 may project directly out of the silicone stopper 2 or may also be provided in the interior of the latter if the layer of the silicone stopper 2 covering the pressure sensor is thin enough that changes in pressure may be transmitted directly onto the pressure sensor.

The silicone stopper 2 is pressed into the ring 3 fluid tight, the ring 3 having a suture ring 3a and a metal subring 3b in the form of a connector. The metal subring 3b may also be connected securely to the suture ring 3a, in particular in a fluid tight manner as well. The cylindrical or conical silicone stopper 2 seals on the inner side of the subring 3b by means of one or a plurality of sealing lips sealing lips running on the circumference. The silicone stopper may have a lid-like projection 2a that when inserted overhangs the subring 3b.

In FIG. 1, one electrode 10, 11 each is visible between two channels 8, 9 running diagonally in the interior of the closing element 2, each of the electrodes 10, 11 having a tip 10a, 11a for anchoring in the tissue of the cardiac wall. These electrodes 10, 11 can pick up electrical pulses from the heart tissue, or, conversely, conduct voltage signals to the cardiac muscle. The electrodes 10, 11 are connected, for example, to a monitoring device by means of electrical lines 12, 13. The device may be an implantable cardioverter/defibrillator and/or a device for cardiac resynchronization therapy (CRT). The signals detected by the electrodes 10, 11 are picked up on the left ventricle. The electrodes 10, 11 may be formed directly using commercially available electrodes that are qualified by their manufacturer for certain cardiac pacemakers.

The pressure sensor 6 may be embodied such that it has a thin membrane, in particular a metal membrane, that projects out of the silicone stopper 2 towards the interior of the heart or that is at least exposed and permits a pressure measurement to be taken in the left ventricle. The pressure sensor 6 may transmit, by means of the transmitter 7, the signals for the detected measurement variables to a monitoring or control unit that itself has a power source and a transmitting/receiving device and that has the function of continuously recording and storing sensor data, and, where necessary, transmitting said sensor data to a receiving device, such as, for example, a mobile telephone or a computer or a control unit external to the body. The control unit may be implanted subcutaneously under the abdominal wall so that the current source/energy storage element of the control unit may be recharged by induction or the current source may be exchanged. All or part of the cable connections in this design may be embodied in a plug-in type manner in order to facilitate exchangeability, or as a fixed connection, which in principle is less susceptible to interference.

The cables 12, 13 connected to the electrodes 10, 11 may project freely out of the openings provided in the silicone stopper and without being connected to the silicone stopper 2 so that the electrodes 10, 11 may be easily inserted and withdrawn. Support elements that support the cables 12, 13 as they exit the stopper may be provided in the silicone body of the stopper 2, wherein these support elements may also be embodied conical and rounded. This is illustrated separately in FIG. 3.

The sealed tightness of the closing element/silicone stopper 2 within the ring 3 is assured in that the sealing lips on the outer circumference of the stopper seal elastically on the metal subring 3b and in that the electrodes 10,11 may be pressed into the channels 8, 9 in the silicone stopper 2 under a slight prestress so that even the channels 8, 9 are sealed against the interior of the heart. The pressure sensor 6 may be glued to or cast with the silicone stopper 2 in a sealing manner.

The suture ring 3a is sutured to the tissue of the cardiac muscle by means of a suture 14, the suture 14 being fixed in the edge region of the suture ring by means of one or a plurality of anchors 15.

FIG. 2 depicts a closing device having a silicon stopper 2 that is tightly arranged in a ring 3, similar to the embodiment illustrated in FIG. 1. Similar to the illustration for FIG. 1, a pressure sensor 6 is embedded in the silicone stopper/closing element 2.

In contrast to the design depicted in FIG. 1, a second pressure sensor 16 is provided and is arranged on the side of the closing element 2 opposing the first pressure sensor 6 and is designed to detect a time-dependent pressure outside of the heart in the body of the patient so that differential pressures and changes that occur outside of the heart in the chest or in the atmosphere may be eliminated by finding the difference in the signals of the pressure sensors 6, 16. The pressure sensor 16 is also connected to the transmitter 7 by means of a cable. Like the pressure sensor 6, the pressure sensor 16 is also embedded in the silicone material of the stopper 2 and/or glued to the silicone stopper.

Provided in the closing element depicted in FIG. 2 are two electrodes 17, 18 that are embodied partly cylindrical in a sleeve-like manner and that are positioned against the cylindrical surface of the stopper 2. Each electrode extends across a sub-section of the circumference of the stopper. The electrodes 17, 18 may also be embedded in the stopper 2 such that the surface of the electrodes 17, 18 is flush with the contour of the stopper 2. The sleeve shapes may also be conical, for example if the stopper 2 tapers conically into a point towards the interior of the heart. In general, however, the stopper 2 is round in cross-section, is essentially cylindrical, and merely has a slightly conical shape for the fit.

The tissue of the cardiac wall 19 is electrically contacted at two different points by means of the electrodes 17, 18 such that the electrodes 17, 18 can pick up electrical pulses from the heart tissue. The electrodes 17, 18 are each connected with crimp connections 17a, 18a to cables 19, 20 that are led in a sealing manner out of the closing element/silicon stopper 2. For mechanical stabilization and for preventing cable rupture, to this end conical cable support elements 21, 22 are cast on the closing body 2.

The electrodes 17, 18 may be used for detecting signals from the cardiac muscle in order to be forwarded to a cardiac pacemaker or cardiograph. In this example, however, it may be specifically provided that the electrode 17 is connected to an implantable cardioverter/defibrillator. The large surface area of the electrode ensures efficient energy distribution in the heart and at the cardiac apex. The somewhat smaller electrode 18 may be connected to a device for cardiac resynchronization therapy (CRT) (left ventricle). This electrode may be positioned inside the ring 3 using a possible rotational orientation of the closing element such that the large electrode is positioned as much as possible on the side facing the septum. This facilitates optimum functioning of the defibrillator.

The design depicted here is particularly suitable for the case in which an implantable cardioverter was already implanted prior to the insertion of the closing element and may be connected to the closing element in a simple manner with electrodes that may be easily placed.

FIG. 3 is a three-dimensional depiction of a silicone stopper 2 as is described in greater detail in FIG. 2, having a suture ring 3a, an electrode 17 integrated into the cylindrical outer contour of the closing element 2, and having, leading out of the stopper 2, three cables 23 (connector to the pressure sensor 6), 24 (connector to a control device for cardiac resynchronization therapy/left ventricle) and 25 (connector for an implantable cardioverter). The cardioverter is depicted symbolically in FIG. 2 using a plug-in connector 26, while the control device for cardiac resynchronization therapy is represented, and likewise depicted symbolically, using a plug-in connector 27 like the plug-in connector 26. The control devices 26, 27 may also be implanted, but it is also possible for them to be integrated into the closing element or for these control devices to be operated outside of the body, the lines 24, 25 in this case then having to be conducted either out of the body of the patient or terminating at an implantable transmitter that transmits the signals to control units arranged outside of the body by means of a non-wired connection.

Cable support elements 21, 22 acting as kink protection elements in the form of conical attachments to the stopper 2 are easily visible in FIG. 3. In one embodiment like that illustrated in FIG. 3, it is also possible to use only a single large surface area electrode 17 that is connected to a cardiac pacemaker that can assume both the function of an implanted cardioverter and that of a control device for cardiac resynchronization therapy. The electrode may then assume both the sensor function when pulses are picked up from the heart tissue and the function of transmitting any energy pulse to the heart tissue (pacing function), and ultimately may also assume the defibrillation function by transmitting a relatively large amount of energy to the heart tissue by means of an electric pulse (defibrillation function). The connection of cables to the specific electrodes 17, 18 by means of crimping sleeves may be particularly favorably configured when the crimping sleeves themselves are part of the electrodes/the electrode sheet in order to limit the number of parts. The cable sheathing should be produced from a silicone in order to optimize compatibility of the materials used and to optimize the connection to the silicone body of the closing element. Crimping sleeves, cable material, and electrode material are coordinated with one another with respect to electrochemical series and comprise, for example, the same material.

FIG. 4 depicts a variant of a closing element 2 in which an integrated pressure sensing unit 20 is inserted into the silicone stopper 2 and has one or a plurality of pressure sensors 6, 16, an energy storage element in the form or a battery or rechargeable battery 28, a preprocessing device 29, for example in the form of a microcontroller, and a transmitter/receiver device 30. The transmitter may support the Bluetooth standard, for example. The pressure sensing device 20 may be cast in the silicone stopper 2 or may be glued therein. The pressure sensors 6, 16 may be combined to create a single differential pressure sensor that is connected to both sides of the closing element.

The source of current/rechargeable battery 28 may be removed from the unit 20 and, for example, implanted under the skin of the patient and connected to the unit 20 by means of a cable in order to permit inductive recharging. This design for the pressure detection unit may be combined with the arrangement of the electrodes according to FIG. 1, 2, or 3. The connectors for the electrodes are omitted in FIG. 4 for the sake of simplicity and ease of understanding; two partially cylindrical sleeve-shaped electrodes 17, 18 are depicted as examples.

Figure 5:
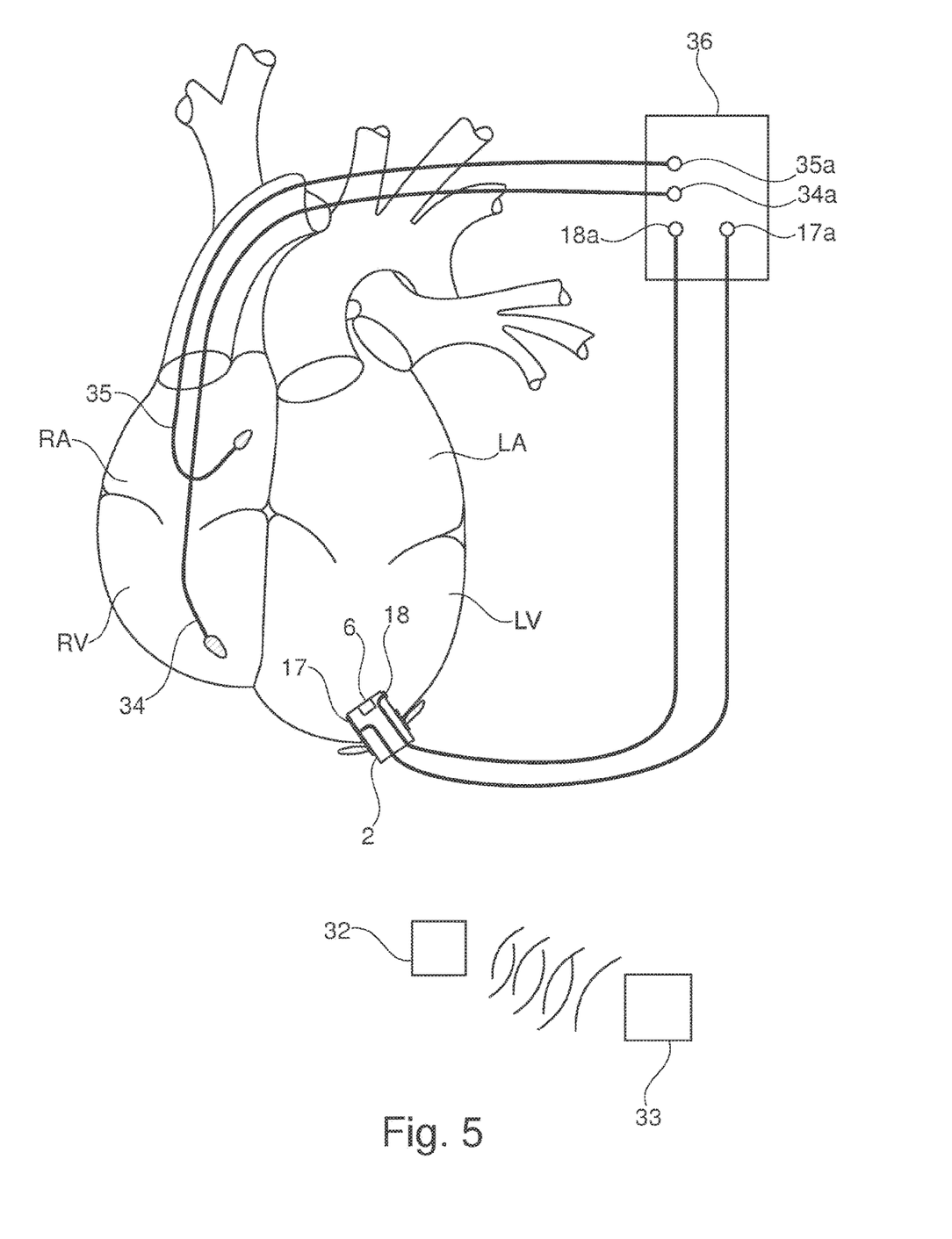
FIGS. 5-10 depict different implantation scenarios for closing devices.

FIG. 5 provides a general view of a connection scheme with a closing device, wherein the closing device may be constructed similar to the closing device depicted in FIG. 2, but not necessarily identical thereto. For the closing element, only the silicone stopper 2, the electrode 17, the electrode 18, and the pressure sensor 6 are shown. In this example, the pressure sensor 6 may be connected to a control device 32 by means of a line (not shown) in the form of a cable or even via a non-wired transmission. The control device 32 itself has a transmitter and a receiver in order to permit communication with external equipment 33, for example in the form of a mobile communication device or a computer.

The various parts of the heart are labeled RA (right atrium), RV (right ventricle), LA (left atrium), LV (left ventricle). Electrode leads with electrodes 34 are conducted via blood vessels for the right ventricle, 35 for the right atrium and terminate in the aforesaid heart chambers. The electrode 34 is connected to a connector 34a of a transvenous cardiac pacemaker 36. The electrode 35 is connected to a connector 35a of the cardiac pacemaker, while the electrode 17 of the closing element 2 is connected to a connector 17a of the cardiac pacemaker and the electrode 18 of the closing element 2 is connected to a connector 18a of the cardiac pacemaker. The transvenous cardiac pacemaker 36 thus obtains the required measurement data in part from electrodes for the closing device and in part from sensors that have been added to the heart independent of the closing device. One of the electrodes 17, 18 may also serve as a pacer electrode.

Figure 6:
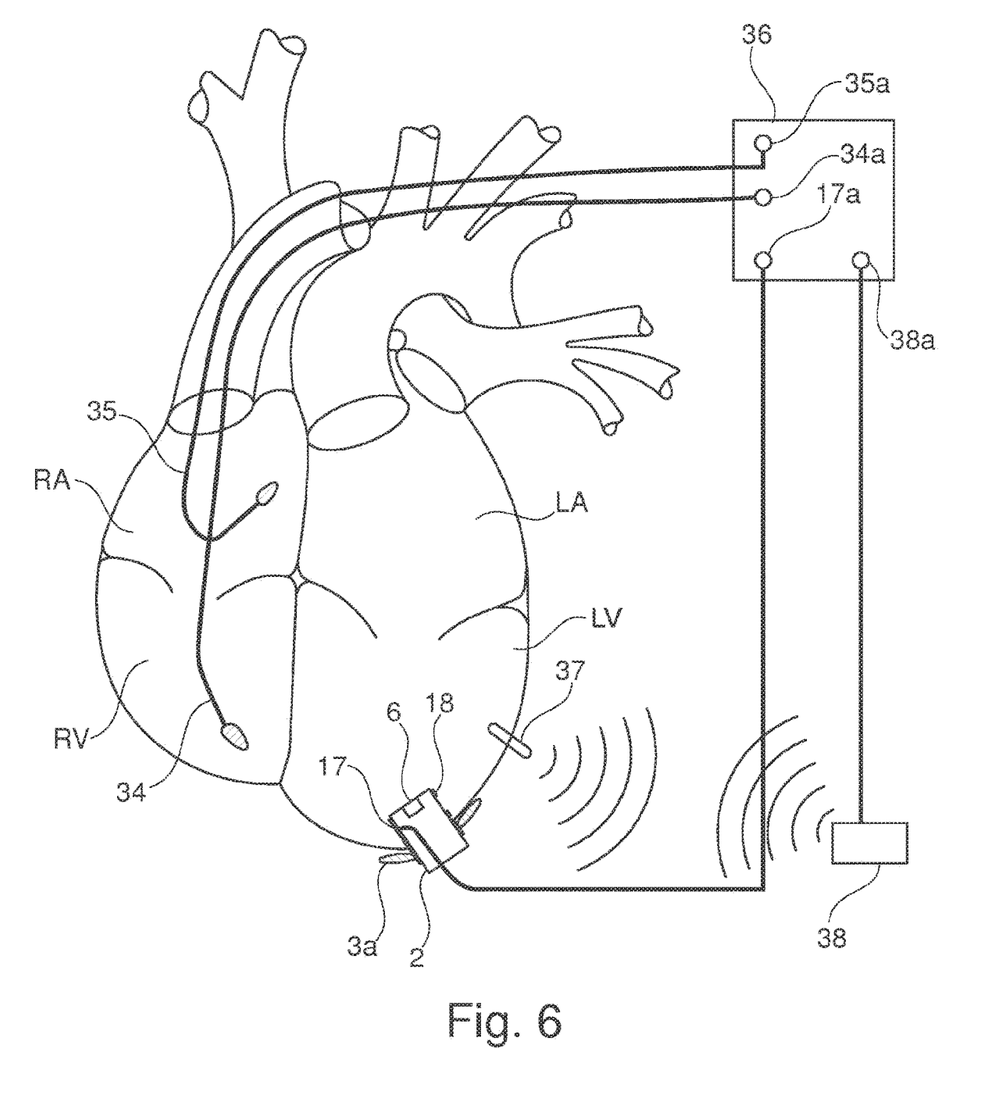

FIG. 6 illustrates a connection design that also has a transvenous cardiac pacemaker 36, the electrodes/sensors 34, 35 being used for cardiac resynchronization therapy. In addition, a sensor 37 is inserted into the left ventricle and transmits via radio signals to a module 38. The module 38 forwards the signals to a connector 38a that is also used for cardiac resynchronization therapy. The data may be preprocessed in the module 38. The module 38 may also be integrated into the cardiac pacemaker 36 as a receiver module. In addition, a connector 17a via which signals for a cardioverter function may conducted from the cardiac pacemaker to the electrode 17, for example for a defibrillation function, is integrated into the cardiac pacemaker.

Figure 7:
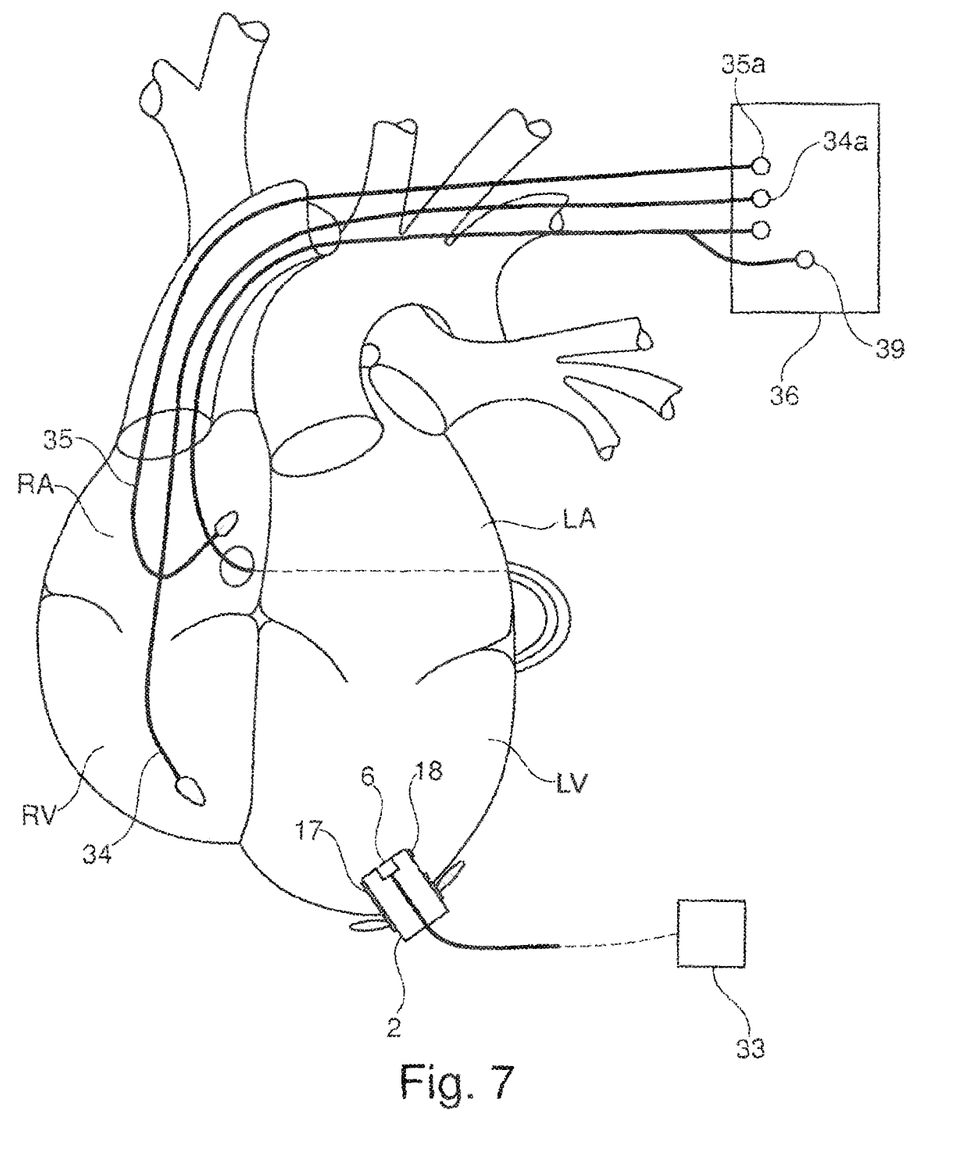

FIG. 7 illustrates a design in which, as in the preceding examples, a sensor from the right atrium is connected to the connector 35a for a cardiac pacemaker and a sensor from the right ventricle is connected to the connector 34a for a cardiac pacemaker. A connector 39 for the cardiac pacemaker is connected to a sensor in the left ventricle via a line that leads through the right atrium via the coronary sinus. The connector 39 may be used, on the one hand, for signals for cardiac resynchronization therapy, and on the other hand for signals of an implant cardioverter for the left ventricle, for example by means of a switch.

The pressure sensor 6 is either connected directly to an external device 33 via a cable or indirectly via a transmitter connected to a cable and via a transmission segment, as already shown in FIG. 5.

Figure 8:
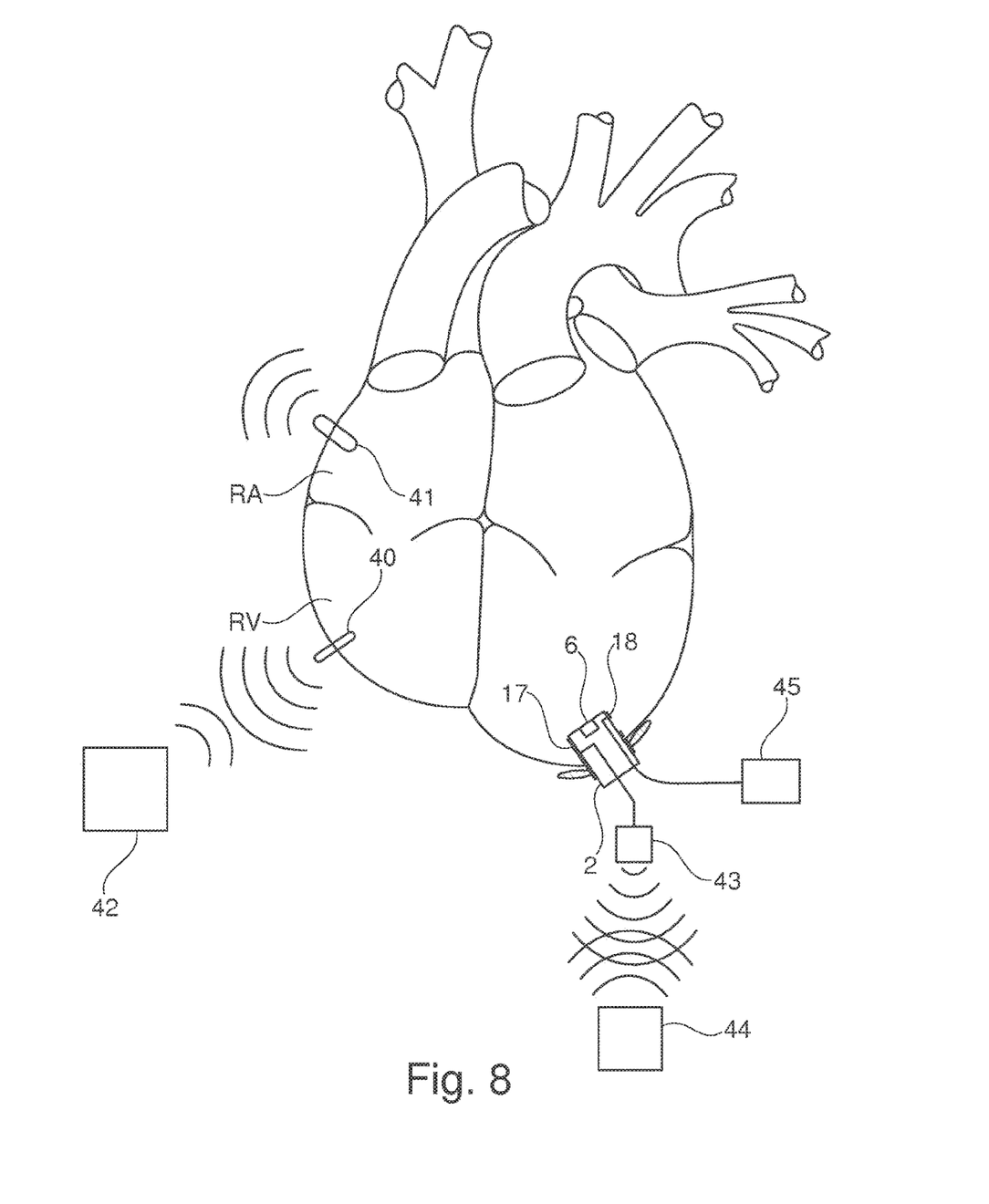

FIG. 8 illustrates a design in which one sensor 40, 41 each is used on the right ventricle RV and on the right atrium RA, the sensors 40, 41 communicating by radio with a cardiac pacemaker 42. The pressure sensor 6 is connected to a transmitter 43 that is connected to an external device 44 via a wireless transmission path. The transmitter 43 may be implantable and arranged in the body separate from the closing element 2, but it may also be integrated into the closing element 2.

The electrode 18 in the closing element 2 is connected separately by means of a cable to a device 45 that may also be implanted and that can assume the function of an implantable cardioverter and/or defibrillator. The device 45 may be connected to the cardiac pacemaker 42, for instance in a wired manner or by means of a non-wired connection. In this variant there is no need for placing lines through blood vessels of the heart.

Figure 9:
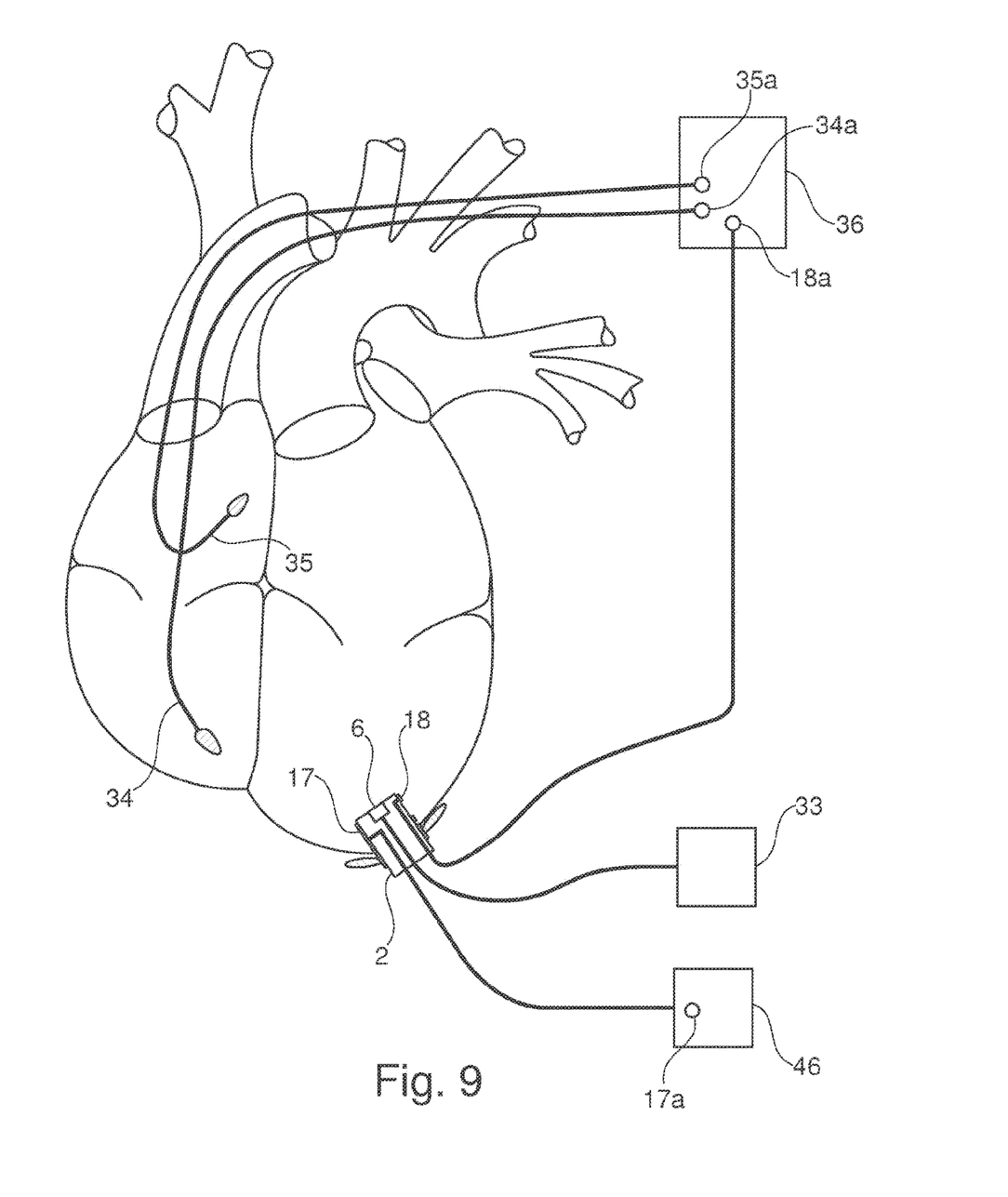

FIG. 9 illustrates a connection design in which two internal sensors 34, 35 in the right ventricle and in the right atrium are connected to a cardiac pacemaker 36 by means of lines that run through blood vessels and that lead to the connectors 34a, 35a. One connector 18a is connected to the electrode 18 on the closing element 2 by means of a line. In addition to satisfying the normal pacing functions, the cardiac pacemaker 36 may satisfy the functions of cardiac resynchronization therapy.

In addition, the electrode 17 is connected by means of a line to the connectors 17a, which is arranged within an implantable cardioverter/defibrillator 46. The defibrillation function is thus satisfied by a device 46 separate from the cardiac pacemaker 36. The pressure sensor 6 is connected in a wired manner to the control device 33.

Figure 10:
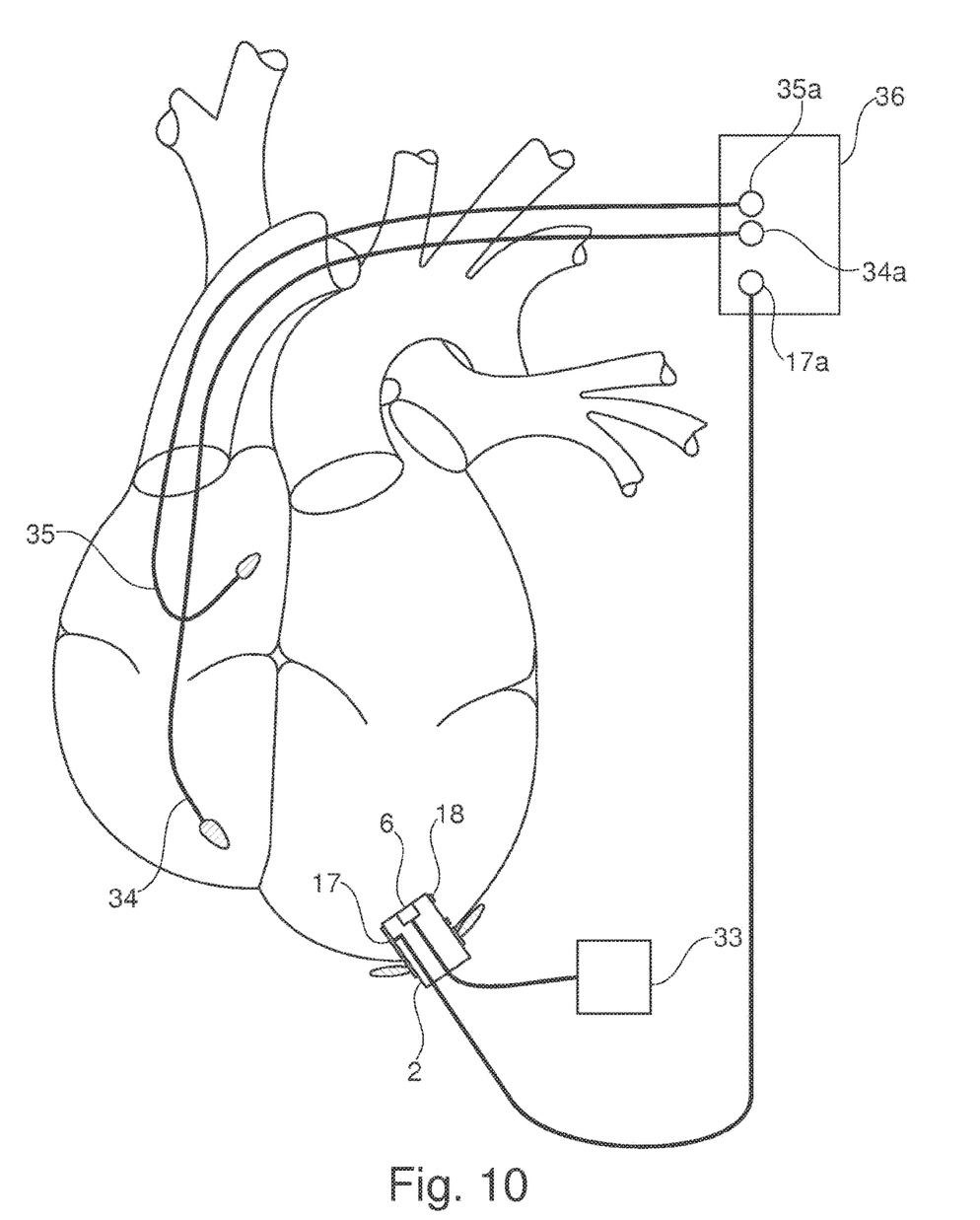

FIG. 10 illustrates a connection design in which sensors/electrodes 34, 35 in the right ventricle and in the right atrium are connected to connectors 34a, 35a of a device 36 and in which, in addition, an electrode 17 of the closing element 2 is connected to a connector 17a in the device 36. The connections are produced in a wired manner, the lines of the sensors 34, 35 traveling through blood vessels of the heart. The pressure sensor 6 is connected to a control device 33.

The device 36 simultaneously satisfies the functions of a cardiac pacemaker for cardiac resynchronization therapy and for conventional stimulation of the heart, and, on the other hand, satisfies the function of an implantable cardioverter that can also execute a defibrillation function via the electrode 17. The connector 17a to the device 36 thus potentially satisfies both functions: on the one hand, conducting an electrical signal from the electrode 17 to the device, and on the other hand emitting an electrical pulse to the electrode 17 via the line. To this end, a switching device that connects the line for the electrode 17 to various inputs or circuits within the device 36 may be provided inside the device 36.

FIGS. 11 and 12 each represent groups of connection designs, each connection design being illustrated in a separate numbered block. Connection designs 50 through 57 are found in FIG. 11, while connection designs 58 through 62 may be seen in FIG. 12. Each of the connection design illustrations is a square comprising four quadrants that in design 50 is labeled with the reference number 66, for example. Within each of the squares 66 the four quadrants should be labeled identically with the reference symbols RA (right atrium), RV (right ventricle), LA (left atrium), and LV (left ventricle). They represent the four chambers of the heart.

One closing element 2 having two electrodes 17, 18 is shown in the left ventricle. The reference numbers are shown only in the design in the block 50, but apply for all of the connection designs illustrated, since the closing element 2 is the same in each of the designs.

Reference number 67 refers to a device that may have the functions of a cardiac pacemaker, the functions of cardiac resynchronization therapy, and the functions of a cardioverter/defibrillator. However the device 67 may also include only individual functions or two of the aforesaid functions, additional functions then be satisfied in a separate device.

The special features and functions for the individual designs are explained briefly in the following. The rectangle 68 shown with a broken line in connection designs 50 through 57 schematically represents the heart of the patient and the sensors and lines arranged inside the heart, including the lines that are conducted through blood vessels of the heart.

FIG. 11:

Design 50: The sensors in the right ventricle RV and atrium RA and the electrode 18 are connected to the device 67 in order to satisfy the functions of cardiac resynchronization therapy. The electrode 17 emits pulses to the heart from the device 67, satisfying the functioning of an implantable cardioverter/defibrillator.

Design 51: This design provides that the sensor 17 is connected to the same connector in the device 67 as the sensor from the right ventricle, said connector serving on the one hand for cardiac resynchronization therapy, and on the other hand for emitting pulses and functioning as a cardioverter/defibrillator. A switching device may also be provided between lines in or on the device 67.

Design 52: In contrast to the design 51, the electrode 17 is directly connected to the sensor in the right ventricle via the cardiac wall. As is the case with the design 51, the sensor in the right ventricle and the electrode 17 may realize the functioning of cardiac resynchronization therapy and also that of a cardioverter/defibrillator.

Design 53: As for the design 50, however the line for the electrode 18 is conducted through the coronary sinus and blood vessels of the heart to the device 67.

Design 54: The electrode 17 is connected to the device 67 via non-wired transmission. Said electrode is for cardiac resynchronization, like the electrode 18 that is connected to the device 67 via a line through the coronary sinus, labeled 69 in the figures. The sensor arranged in the right ventricle serves only the functioning of the cardioverter/defibrillator, while the sensor in the right ventricle serves resynchronization therapy.

Design 55: According to this design, the line for the electrode 18 is again connected to the device 67 by means of a line through the coronary sinus and serves for resynchronization therapy, just like the sensor in the right atrium. The electrode 17 is connected to the device 67 by means of a line that penetrates the cardiac wall and, like the sensor in the right ventricle, serves the function of cardioverter/defibrillator.

Design 56: This design provides that the sensors in the right ventricle and in the right atrium are connected to the device 67 by means of lines, while one or a plurality of the electrodes 17, 18 are connected to the device 67 by means of a transmitter, integrated into the closing element 2, and a receiver 70.

Design 57: According to this design, the sensors in the right atrium and right ventricle are connected to the device 67 by means of lines, and the electrode 18 on the closing element is also connected to the device 67 by means of a line conducted through the coronary sinus. In addition, a line is depicted that connects the pressure sensor on the closing element to a control device 71.

FIG. 12:

Design 58: According to this design, the sensors in the right ventricle and right atrium are connected to the device 67 in a wired manner, as are the electrodes 17 and 18, the electrode 17 in particular satisfying the function of the cardioverter or defibrillator.

Design 59: In contrast to the design 58, in the design 59 it is provided that the electrode 17 is connected by means of a line to the line of the sensor in the right ventricle and together therewith is connected to the device 67. The two electrodes function in particular as cardioverter/defibrillator. The stricken connector to the device 67 is not required.

Design 60: According to this concept, the electrode arranged in the right atrium is connected to the device 67 via a line, as is the electrode 18 of the closing element 2. The electrode 17 of the closing element is connected to the device 67 by means of a line that runs transseptal through the right ventricle.

Design 61: According to the design 61, the sensors in the right atrium and right ventricle are connected to the device 67, the electrode 17 of the closing element is connected to the device 67 by means of a transseptal line leading through the right ventricle, and the electrode 18 of the closing element is also connected to the device 67 by means of a line conducted through the coronary sinus.

Design 62: According to the design 62, the sensor in or on the right atrium is connected to the device 67 by means of a line.

To clarify the use of and to hereby provide notice to the public, the phrases "at least one of <A>, <B>, . . . and <N>" or "at least one of <A>, <B>, . . . <N>, or combinations thereof" or "<A>, <B>, . . . and/or <N>" are defined by the Applicant in the broadest sense, superseding any other implied definitions hereinbefore or hereinafter unless expressly asserted by the Applicant to the contrary, to mean one or more elements selected from the group comprising A, B, . . . and N. In other words, the phrases mean any combination of one or more of the elements A, B, . . . or N including any one element alone or the one element in combination with one or more of the other elements which may also include, in combination, additional elements not listed. Unless otherwise indicated or the context suggests otherwise, as used herein, "a" or "an" means "at least one" or "one or more."

The application includes the following aspects, inter alia:

1. A closing device (1) for an opening (5) in the heart of a patient, having a ring (3, 3a, 3b) that can be fastened to the body tissue of the heart in the region of the opening and that has a ring opening and having a closing element (2) that can be inserted into the ring opening, characterized in that the closing element (2) has at least one integrated sensor (6, 10, 11, 16, 17, 18) and/or at least one integrated actuator (17, 18).
2. The closing device according to aspect 1, characterized in that at least one integrated sensor (6, 16) is designed for detecting a time-dependent pressure.
3. The closing device according to aspect 2, characterized in that the closing element (2) has at least one pressure sensor (6) that detects a pressure on a first outer side of the closing element, and in particular has a second pressure sensor (16) that detects a pressure on a second outer side, the closing element being designed such that when the closing element is in the closing position, the first outer side faces the interior of the heart and the second outer side faces the exterior of the heart.

4. The closing device according to aspect 1, 2, or 3, characterized in that the closing element (2) has a sensor (10, 11, 17, 18) or at least two sensors for detecting a voltage signal.
5. The closing device according to aspect 1, 2, 3, or 4, characterized in that the closing element (2) has at least one, in particular at least two, electrodes (10, 11, 17, 18) that form a surface region of the closing element (2), in particular a cylindrical or partly cylindrical surface region of the closing element, in at least one or at least two subregions.
6. The closing device according to aspect 1, 2, 3, or 4, characterized in that the closing element (2) has at least one, in particular at least two, electrodes (10, 11, 17, 18) that each have a first part arranged inside the closing element and a second part projecting out of the closing element, each second part having a tip (10a, 11a).
7. The closing device according to aspect 1, 2, 3, 4, 5, or 6, characterized in that an actuator integrated into the closing element has an electrode (10, 11, 17, 18) that may be acted upon with a time-dependent voltage signal and in particular may be connected to a control device (26, 27, 33, 36, 43, 45).
8. The closing device according to aspect 1, 2, 3, 4, 5, 6, or 7, characterized in that at least one sensor and/or at least one actuator (6, 10, 11, 16, 17, 18) may be connected to a control or monitoring device (26, 27, 33, 36, 43, 45) by means of a cable or a non-wired transmitting device, directly or by means of a preprocessing device (32, 38, 439 integrated into the closing device, in particular into the closing element.
9. The closing device according to aspect 1, 2, 3, 4, 5, 6, 7, or 8, characterized in that at least one sensor and/or at least one actuator (6, 10, 11, 16, 17, 18) may be connected to an energy storage element (28) that is either implanted in the body of the patient or is provided outside the body of the patient.
10. The closing device according to aspect 9, characterized in that the energy storage element (28) is implanted into the closing element (2) or into an implantable/implanted control or monitoring device (26, 27, 33, 36, 43, 45) or is implanted as a module in the body of the patient.
11. The closing device according to aspect 10, characterized in that the energy storage element (28) is designed and arranged such that it may be recharged by means of an induction device arranged outside of the body of the patient.
12. An implantable device having a closing device according to any of the preceding aspects and in particular having an energy storage element (28) and/or having a monitoring device and/or having a control device (26, 27, 33, 36, 43, 45).
13. The implantable device according to aspect 12, characterized in that it has a cardiac pacemaker (36) and/or defibrillator (43, 45) that is connected to at least one electrode integrated into the closing element.
14. A method for operating an implantable device according to aspect 12 or 13, characterized in that, when implanted, a pressure curve in a heart ventricle, in particular the left ventricle, is measured by means at least one pressure sensor (6, 16) integrated into the closing element (2) and from this an end diastolic filling pressure is determined, and/or in that, when implanted, a signal or an energy pulse is emitted to the cardiac muscle by means of at least one electrode (17, 18) integrated into the closing element (2).

The invention claimed is:

1. A closing device for an opening in the heart of a patient, the closing device comprising:
a ring configured to be fastened to the body tissue of the heart in a region of the opening, the ring comprising a ring opening; and
a closing element comprising a stopper that is configured to be pressed into the ring opening and configured to seal the ring opening, wherein the closing element comprises at least one integrated sensor that is disposed in a hollow chamber of the closing element, wherein the at least one integrated sensor includes at least one pressure sensor configured to detect a pressure on a first outer side of the closing element and wherein the closing element has a second pressure sensor that detects a pressure on a second outer side, the closing element being designed such that when the closing element is in the closing position, the first outer side faces the interior of the heart and the second outer side faces the exterior of the heart.

2. The closing device according to claim 1, wherein the at least one integrated sensor includes at least two integrated sensors configured to detect a time-dependent pressure.

3. The closing device according to claim 1, wherein the at least one integrated sensor includes at least two sensors configured to detect a voltage signal.

4. The closing device according to claim 3, wherein a plurality of electrodes form cylindrical surface regions of the closing element.

5. The closing device according to claim 3, wherein the at least two detectors are arranged to detect a voltage potential in the tissue of the heart or to transmit voltage pulses to the heart tissue.

6. The closing device according to claim 1, wherein the at least one integrated sensor includes at least two sensors connected to a control or monitoring device, directly or by means of a preprocessing device integrated into the closing device, by means of a cable or a non-wired transmission device.

7. The closing device according to claim 6, wherein the preprocessing device is integrated into the closing element.

8. The closing device according to claim 1, wherein the at least one integrated sensor includes at least two sensors configured to connect to an energy storage element that is either implanted in the body of the patient or is provided outside the body of the patient.

9. The closing device according to claim 8, wherein the energy storage element is integrated into the closing element or into an implantable/implanted control or monitoring device or is implanted as a module in the body of the patient.

10. The closing device according to claim 9, wherein the energy storage element is designed and arranged such that it may be recharged by means of an induction device arranged outside of the body of the patient.

11. The closing device according to claim 1, wherein the ring is formed by a suture ring.

12. An implantable device comprising:
a closing device for an opening in the heart of a patient, the closing device including a ring and a closing element, wherein the ring can be fastened to the body tissue of the heart in a region of the opening, the ring has a ring opening, and the closing element comprises a stopper that can be pressed into the ring opening in order to seal the ring opening, wherein the closing element has at least one integrated sensor; and
an energy storage element, a monitoring device, and/or a control device.

13. A method for operating an implantable device, the implantable device comprising a closing device for an opening in the heart of a patient, the closing device comprising a ring and a closing element, wherein the ring is configured to be fastened to the body tissue of the heart in a region of the opening, the ring comprising a ring opening, and the closing element comprising a stopper configured to be pressed into the ring opening and configured to seal the ring opening, wherein the closing element comprises at least one pressure sensor implanted into the closing element, the method comprising:
- measuring, by the at least one pressure sensor, a pressure curve in a heart ventricle; and
- determining an end diastolic filling pressure from the measured pressure curve.

14. The method of claim 13, wherein the heart ventricle is a left ventricle.

* * * * *